(12) United States Patent
Hsu et al.

(10) Patent No.: US 11,384,326 B2
(45) Date of Patent: Jul. 12, 2022

(54) SELECTIVE PARTICLES TRANSFER FROM ONE DEVICE TO ANOTHER

(71) Applicant: NATIONAL HEALTH RESEARCH INSTITUTES, Zhunan Town (TW)

(72) Inventors: Chia-Hsien S. Hsu, Zhunan Town (TW); Ching-Hui Lin, Zhunan Town (TW); Duane S. Juang, Zhunan Town (TW); Hao-Chen Chang, Zhunan Town (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 511 days.

(21) Appl. No.: 15/777,501

(22) PCT Filed: Nov. 18, 2016

(86) PCT No.: PCT/US2016/062948
§ 371 (c)(1),
(2) Date: May 18, 2018

(87) PCT Pub. No.: WO2017/087906
PCT Pub. Date: May 26, 2017

(65) Prior Publication Data
US 2018/0334647 A1 Nov. 22, 2018

Related U.S. Application Data

(63) Continuation of application No. 15/159,712, filed on May 19, 2016, now Pat. No. 10,000,732.
(Continued)

(51) Int. Cl.
*C12M 3/06* (2006.01)
*B01L 3/00* (2006.01)
(Continued)

(52) U.S. Cl.
CPC ....... *C12M 23/16* (2013.01); *B01L 3/502707* (2013.01); *B01L 3/502715* (2013.01);
(Continued)

(58) Field of Classification Search
CPC ........ C12Q 2600/158; C12Q 2600/118; C12Q 2600/112; C12Q 1/20; G01N 2800/50;
(Continued)

(56) References Cited

U.S. PATENT DOCUMENTS 5,110,556 A * 5/1992 Lyman ................ B01L 3/50255
356/246
5,578,269 A * 11/1996 Yaremko .............. G01N 35/025
210/361

(Continued)

*Primary Examiner* — Dean Kwak
(74) *Attorney, Agent, or Firm* — Muncy, Geissler, Olds & Lowe, P.C.

(57) ABSTRACT

A target particle transferring device is disclosed, which comprises: (a) a substrate with a thickness of T and a width of W, having top and bottom portions, the top portion having a top surface and the bottom portion having a bottom surface; (b) a notch structure formed in the bottom portion of the substrate, comprising: a groove with a width of W1, located at a distance oft below the top surface of the substrate, wherein the groove is formed in the bottom portion from the bottom surface extending toward the top portion; and (c) a target substrate portion with a width of W2 and a thickness of T, located in the top and bottom portions of the substrate and being surrounded by the groove. Methods of transferring a target particle from one device to another is also disclosed.

2 Claims, 6 Drawing Sheets

Related U.S. Application Data

(60) Provisional application No. 62/258,174, filed on Nov. 20, 2015.

(51) Int. Cl.
  *C12M 1/32* (2006.01)
  *C12M 1/00* (2006.01)
  *C12M 1/26* (2006.01)
  *C12M 1/16* (2006.01)

(52) U.S. Cl.
  CPC ....... *B01L 3/502761* (2013.01); *C12M 1/165* (2013.01); *C12M 1/265* (2013.01); *C12M 23/12* (2013.01); *C12M 23/32* (2013.01); *C12M 23/50* (2013.01); *C12M 29/00* (2013.01); *C12M 33/00* (2013.01); *C12M 33/04* (2013.01); *C12M 99/00* (2013.01); *B01L 2200/0647* (2013.01); *B01L 2300/0829* (2013.01); *B01L 2300/0887* (2013.01); *B01L 2300/12* (2013.01); *B01L 2300/16* (2013.01)

(58) Field of Classification Search
  CPC ....... G01N 2800/52; G01N 2333/4703; G01N 2800/00; G01N 33/5008; G01N 33/566; G01N 33/573; G01N 33/6872; G01N 33/6893; B01L 2300/0829; B01L 3/502715; B01L 2200/0647; B01L 2300/0887; B01L 2300/12; B01L 2300/16; B01L 3/502707; B01L 3/502761; B01L 2300/0636; B01L 2300/0819; B01L 2300/0848; B01L 2300/087; B01L 2300/123; B01L 3/5085; C12M 1/165; C12M 1/265; C12M 23/12; C12M 23/16; C12M 23/32; C12M 23/50; C12M 29/00; C12M 33/00; C12M 33/04; C12M 99/00

See application file for complete search history.

(56) References Cited

U.S. PATENT DOCUMENTS

| | | | |
|---|---|---|---|
| 7,708,881 B2* | 5/2010 | Yu | B01L 3/502753 210/222 |
| 2003/0040087 A1 | 2/2003 | Kim et al. | |
| 2007/0015277 A1 | 1/2007 | Hattori et al. | |
| 2007/0178441 A1 | 8/2007 | Li | |
| 2008/0009063 A1 | 1/2008 | Okano et al. | |
| 2014/0162374 A1* | 6/2014 | Jorgensen | G01N 35/00732 436/501 |
| 2015/0275172 A1 | 10/2015 | Tabata et al. | |

* cited by examiner

SELECTIVE PARTICLES TRANSFER FROM ONE DEVICE TO ANOTHER

FIELD OF THE INVENTION

The present invention relates generally to designs for a target particle transfer from one device to another device and more specifically to a target isolated cell transfer from one substrate to another.

BACKGROUND OF THE INVENTION

Transferring cells from one device to another is essential in many cell-based applications including cells passaging, cell expansion, and cell analysis, all of which require that cells be removed from the original device and transported to another device suitable for down-steam use. In some applications such as mono-colony producing there is a need for transferring only those cells of interest from a larger group of heterogeneous cells. Thus, a selective cell transfer method is required. Traditionally, this selective cell transfer is usually done by using a glass capillary tube or micropipette to pick up the cells of interest in a conventional cell culture dish or well plate. These methods have several limitations: Firstly, they are very low throughput when they are performed manually because the capillary or micropipette has to be precisely placed near the target cell(s) under microscopic observations by the operator to ensure that only the target cell(s) is transferred. Secondly, these methods cannot be used where the cells are not readily accessible (e.g., when cells are located and enclosed within a microchannel). Thirdly, they run a high risk of causing cell damage, as the cells are subjected to a strong shear stress from the suction force introduced by the micropipette. And lastly, they require that the cell of interest be either in a non-adherent state, or is dissociated from the substrate via enzymatic treatment. Adherent cells cannot be directly retrieved via a micropipette as this would result in cell membrane damage. Laser capture microdissection is another method that can also be used for selective cell transfer. It utilizes a laser mounted on a microscope to selectively dissect out target cells from a given sample. However this method requires expensive equipments and use of a special substrate.

SUMMARY OF THE INVENTION

In one aspect, the invention relates to a target particle transferring device, which comprises:
 (a) a substrate with a thickness of T and a width of W, having a top portion with a thickness of t and a bottom portion with a thickness of T-t immediately adjacent to the top portion, the top portion having a top surface and the bottom portion having a bottom surface opposite to the top surface;
 (b) a notch structure formed in the bottom portion of the substrate, comprising: a groove with a width of W1, located at a distance of t below the top surface of the substrate, wherein the groove is formed in the bottom portion from the bottom surface extending toward the top portion; and
 (c) a target substrate portion with a width of W2 and a thickness of T, located in the top and bottom portions of the substrate and being surrounded by the groove; wherein the substrate width W is greater than the summation of the width W2 of the target substrate portion and the double groove width 2×W1.

In one embodiment, the groove is a circle-shaped or C-shaped groove.

In another embodiment, the substrate is made out of a hard material. The hard material may be polymethyl methacrylate (PMMA) or polycarbonate (PC).

In another embodiment, the target particle transferring device further comprises a particle of interest attached onto the target substrate portion.

In another embodiment, the top surface of the substrate is non-flat, and the substrate comprises multiple wells evenly spaced apart and spanning the top and bottom portions of the substrate, each well having a depth of d that is smaller than the substrate thickness T.

In another embodiment, the target particle transferring device further comprises a particle of interest, wherein the particle is inside a well and attached onto the target substrate portion.

In another embodiment, the particle is enclosed within a closed chamber.

In another embodiment, the particle is at least one selected from the group consisting of a cell, a virus, a bacteria, and a microparticle. In another embodiment, the target particle transferring device comprises a plurality of the notch structures, or comprises one or more notch structures, or at least one notch structure.

In another embodiment, the target particle transferring device further comprises a hollow structure spanning the bottom portion of the substrate and the top portion of the substrate, wherein the width of the hollow structure spanning the top portion of the substrate is W2, and the width of the hollow structure spanning the bottom portion of the substrate is the summation of 2×W1 and W2, and the maximum depth of the hollow structure is T.

In another aspect, the invention relates to a method of transferring a target particle from one device to another device, which comprises:
 (i) providing a target particle transferring device of the invention;
 (ii) using a tool to remove the target substrate portion away from the device along with the particle attached thereto; and
 (iii) placing the removed target substrate portion along with the particle attached thereto into a container.

In another aspect, the invention relates to a method of transferring a target particle from one device to another device, which comprises:
 (i) providing a device comprising a substrate with a thickness of T and a width of W, having a top portion and a bottom portion immediately adjacent to the top portion, the top portion having a top surface and the bottom portion having a bottom surface opposite to the top surface;
 (ii) identifying one area of the substrate that has a particle of interest attached onto the substrate as a target substrate portion, wherein the target substrate portion has a width of W2 and a thickness of T and is located in the top and bottom portions of the substrate;
 (iii) fabricating a notch structure, the notch structure being formed in the bottom portion of the substrate and comprising:
 a groove with a width of W1, located at a distance of t below the top surface of the substrate, wherein the groove is formed in the bottom portion from the bottom surface extending toward the top portion and surrounds the target substrate portion;

(iv) removing the target substrate portion away from the device along with the particle of interest attached thereto by using a tool; and (iii) placing the removed target substrate portion along with the particle attached thereto into a container.

In one embodiment, the tool is adapted for gripping the target substrate portion from the groove of the notch structure.

Further in another aspect, the invention relates to a method of transferring a target particle from one device to another device, which comprises:

(i) providing a device comprising a substrate with a thickness of T and a width of W, having a top portion and a bottom portion immediately adjacent to the top portion, the top portion having a top surface and the bottom portion having a bottom surface opposite to the top surface; wherein the substrate is made out of a soft material.

(ii) identifying one area of the substrate 306 that has a particle of interest attached onto the substrate as a target substrate portion, wherein the target substrate portion has a width of W2 and a thickness of T and is located in the top and bottom portions of the substrate;

(iii) removing the target substrate portion away from the device along with the particle of interest attached onto the target substrate portion by using a tool; and (iv) placing the removed target substrate portion along with the particle attached thereto into a container.

The step of removing does not involve an operation under a microscopic observation.

In one embodiment, the top surface of the substrate is non-flat, and the substrate comprises multiple wells evenly spaced apart and spanning the top and bottom portions of the substrate, each well having a depth of d that is smaller than the substrate thickness T, wherein the particle of interest is inside a well and attached onto the target substrate portion.

In another embodiment, the tool is adapted for punching out only the target substrate portion with the particle of interest attached thereto from the top surface of the substrate.

In another embodiment, the container contains a particle detachment solution to release the particle from the removed target substrate portion.

In another embodiment, the top surface is flat.

In another embodiment, the soft material is polydimethylsiloxane (PDMS).

In another embodiment, the substrate is made of a plastic material.

In another embodiment, the target particle transferring device is a bottom culture dish.

In another embodiment, the device of the invention further comprise a cover substrate, and particles are enclosed within a chamber or a channel.

In another embodiment, the cover substrate that is immediately above the target particles of interest is punched out together with the target substrate along with the particles of interest attached onto the target substrate.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
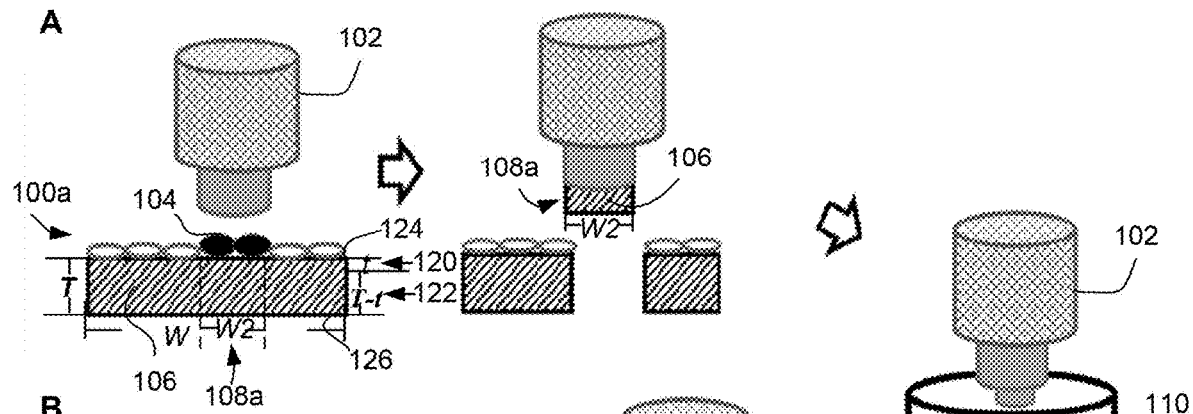
FIG. 1 is a schematic drawing showing an operation procedure of transferring particles from a soft material device to another container. Target particles on a flat substrate in device (A, C) or on a compartment substrate in device (B, D) are selectively picked out and transferred by a puncture to another container. The devices in (A-D) are made out of soft material substrate.
Figure 1:
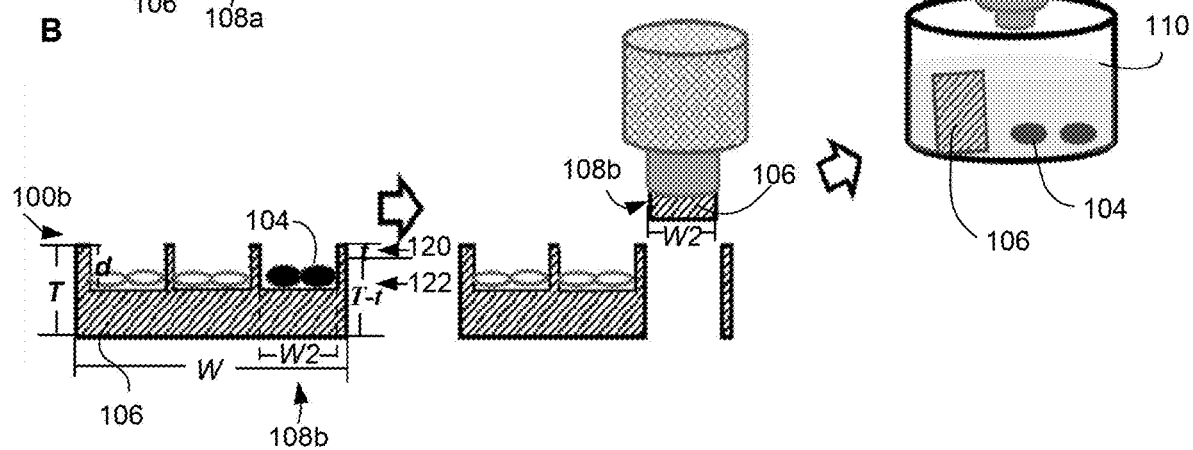
Figure 1:
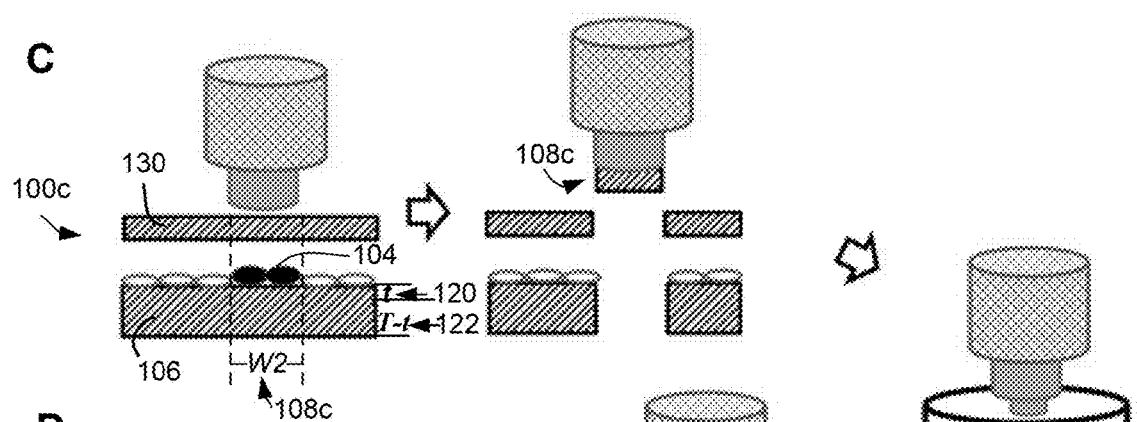
Figure 1:
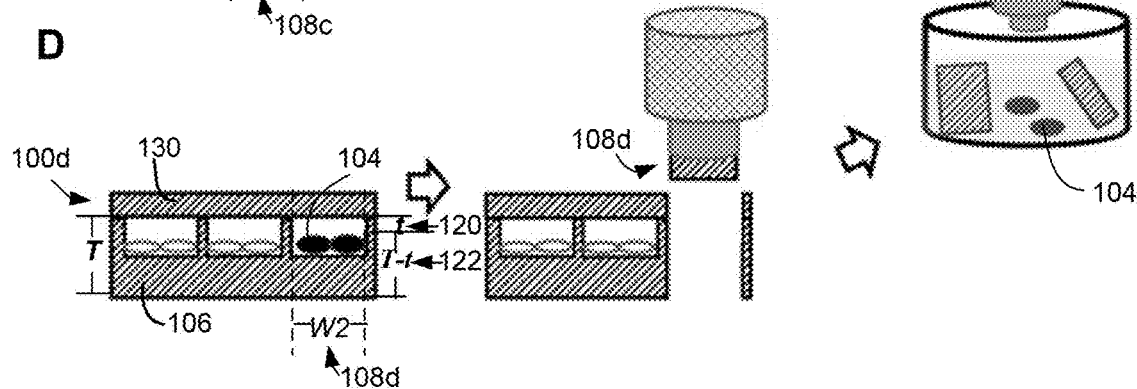

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, when a number or a range is recited, ordinary skill in the art understand it intends to encompass an appropriate, reasonable range for the particular field related to the invention.

The invention relates to device designs and methods for a cell transfer which does not require high-precision positioning operation and can be used for transferring cells which are located inside a closed space such as in a microchannel or a microchamber. This method transfers cells by fracturing and removing a cell-attached portion of the device. We demonstrate that this method can be used for cell transfer in devices made in PDMS (soft) material as well as plastic (hard) material.

As used herein, a target substrate is surrounded by a groove. The width W2 of a target substrate is an equivalent to the diameter of the target substrate (FIG. 4A, top view).

Where a groove is circle-ring shaped or C-shaped, the width W1 of the circle-ring shaped or C-shaped groove is defined as the distance or space between the target substrate and the remaining portion of the bottom substrate immediately adjacent to the groove (FIG. 4A, top view).

The notch as used herein is defined as a structure comprising a target substrate and a groove surrounding the target substrate as shown in FIG. 4A, top view, which is a view from the top of a notch structure. Thus, the width (or a diameter) of a notch structure is W1+W2+W1.

EXAMPLES

Exemplary instruments, apparatus, methods and their related results according to the embodiments of the present invention are given below.
Methods
Device Fabrication Soft material device: The multi-well devices were made of polydimethylsiloxane (PDMS) using soft lithography techniques. Briefly, negative photoresist (SU-8, Micro-Chem, Newton, Mass., USA) was photolithographically patterned on silicon wafers to create masters. The height of the SU-8 features was measured using a scanning laser profilometer (VK-X 100, KEYENCE, Japan). The masters were then used as molds, on which Sylgard 184 (Dow corning, USA) PDMS pre-polymer mixed with its cross-linker at 10:1 ratio was poured and allowed to cure in a conventional oven at 65° C. for 3 hours. The cured PDMS replicas were peeled off from the molds.

Hard material device: the patterns of the notch ring structure were designed by using AutoCAD software and then converted to a 3D CAD file using Solidworks software. The notch ring structure was made on the bottom surface of the substrate of a tissue culture dish (BD falcon™) by using a carving machine (Roaland, EGX-400). The circular notches were 200, 300 and 400 μm in width and 400, 600, 800 μm in depth. The central circle was 2 mm in diameter. A pair of tweezers was used to pick up the substrate portion of a target area by inserting the tweezers' tips into the ring notch to gripe the target area substrate and remove it from the device.
Cell Culture and Maintenance Cancer cell lines—human lung cancer A549 was maintained in DMEM basal medium (Gibco, USA) with 10% fetal bovine serum (FBS, Biowest, France) and 1% antibiotics. The cell cultures were passaged using a recombinant enzyme ACCUMAX™ (Innovative cell technology, USA) under the manufacture's standard protocol at 70-80% confluence.
Transferring and Releasing of Cell Colonies from Culture Well After culture, cells transferring and releasing were performed by punching out cell-containing plugs from the PDMS device. The cell transferring process is illustrated in FIG. 1. Firstly, the locations of the target colonies were marked after examining all the wells of the culture device. Secondly, the PDMS device containing the culture wells was submerged in a culture medium-filled dish. Thirdly, each culture well that contains target cells was punched out from the device with a tissue puncher and subsequently transferred to a 96 well-plate well containing 30 μL of ACCUMAX™ solution. Fourthly, after all the target cells had been transferred, the 96 well-plate was kept in a biohood at the room temperature for 10 min, followed by agitating the 96 well-plate with a well-plate shaker for 1 min at the room temperature. Finally, 150 μL of a culture medium was added into each well and the 96 well-plate was placed into a standard cell culture incubator at 37° C. and 5% CO2. After 1 day of culture, the culture medium in the well-plate was replaced with a fresh culture medium to completely remove ACCUMAX™ in the cell culture medium.
Result
Target Cell Harvest and Release in a 96-Well Plate after Cell Transfer from a PDMS Device FIG. 1 is a schematic drawing showing an operation procedure of transferring particles 104 from a soft material device to another container. Target particles 104 on a flat substrate 108a or 108c in device 100a or 100c (A, C) or on a compartment substrate 108b or 108d in device 100b or 100d (B, D) are selectively picked out and transferred by a puncture 102 to another container 110. Device 100c and device 100d (cross-section of a partial device shown) each further comprise a cover substrate 130, in which particles 104 are enclosed within a chamber or a channel. For example, device 100c or 100d may be a device with microchannel or a device with microchamber, and particles are thus located inside a closed channel/chamber (C & D).

The device 100 (100a, 100b, 100c, 100d) are made out of soft material substrate 106. A method for transferring a target cell (or particle) of interest 104 comprises the following steps:

(i) providing a device 100 (100a, 100b, 100c, or 100d), which comprises a substrate 106 with a thickness of T and a width of W, having a top portion 120 and a bottom portion 122 immediately adjacent to the top portion, the top portion 120 having a top surface 124 and the bottom portion 122 having a bottom surface 126 opposite to the top surface 124; wherein the substrate 106 is made out of a soft material 106.

(ii) identifying one area of the substrate that has a cell (or particle) of interest 104 attached onto the substrate 106 as a target substrate portion 108a, 108b, 108c, or 108d, wherein the target substrate portion 108 has a width of W2 and a thickness of T and is located in the top 120 and bottom 122 portions of the substrate 106;

(iii) removing the target substrate portion 108a, or 108b away from the device along with the cell of interest 104 attached onto the target substrate portion 108a, 108b, 108c, or 108d by using a tool 102; and (iv) placing the removed target substrate portion 108a, 108b, 108c, or 108d along with the cell 104 attached thereto into a container 110 containing a medium.

The cover substrate 130 immediately above the target particles 104 in device 100c is punched out together with the target substrate 108c onto which the particles 104 are attached.

Figure 2:
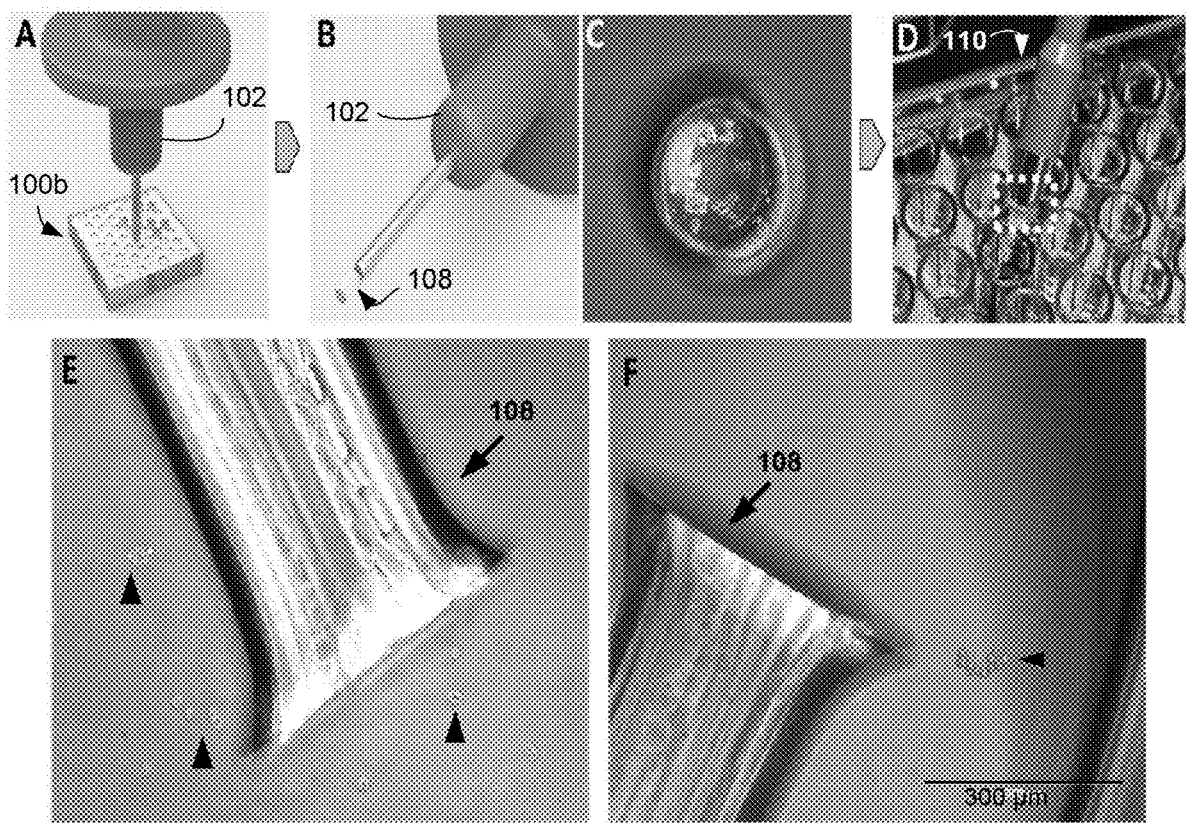
FIG. 2 demonstrates a cell transfer from a PDMS microwell device to a 96-well plate. (A & B) Target cells were harvested from a culture well using a puncher. (C) The punched-out PDMS plug contains target cells. (D) The cell-containing plugs were put into a well of a 96-well plate. (E & F) The released cells (arrowheads) and the PDMS plug (arrows) in a well of a 96 well-plate.

FIG. 2 shows a demonstration. After the cells had been cultured in a multi-well PDMS device 100b, the substrate portion 108 of a target well was punched out using a puncher 102 (A). The punched-out plug 108 contains target cells (B & C). Subsequently, each plug 108 was transferred to a 96 well-plate well containing 30 μL of ACCUMAX™ solution (D). The target cells were then released from the plug (E & F, black arrows) to the well by the ACCUMAX™ treatment. The cells that had just been released and had not yet attached spread in the well are shown (E & F, arrowheads).

A Cell Transfer Strategy with a Notch Ring Structure

Figure 3:
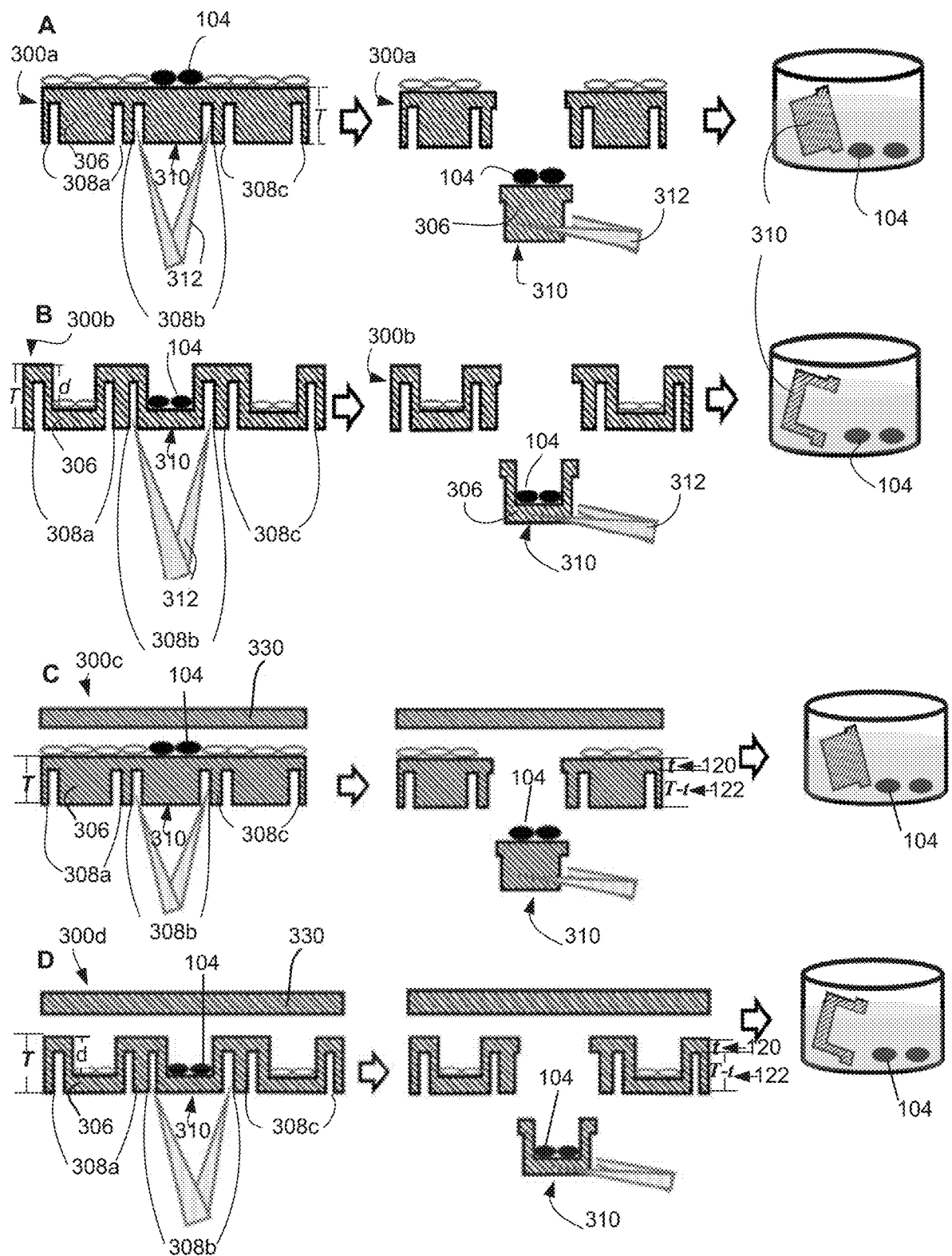
FIG. 3 is a schematic drawing showing substrate designs for particle transfers (with a notch ring structure and operation procedure for a device made of hard plastic martial 306. The target particles 104 on a flat substrate in device (A, C) or on a multi-well substrate (B, D) in device are selectively pick out and transferred by inserting a pair of tweeters to gripe a portion of the substrate, break it and remove it from device. Side-view of the device. A tool (e.g., a pair of tweeters) is to hold the target unit and separate it from the rest of the substrate. The substrate of the device is made out of a hard material.
Figure 4:
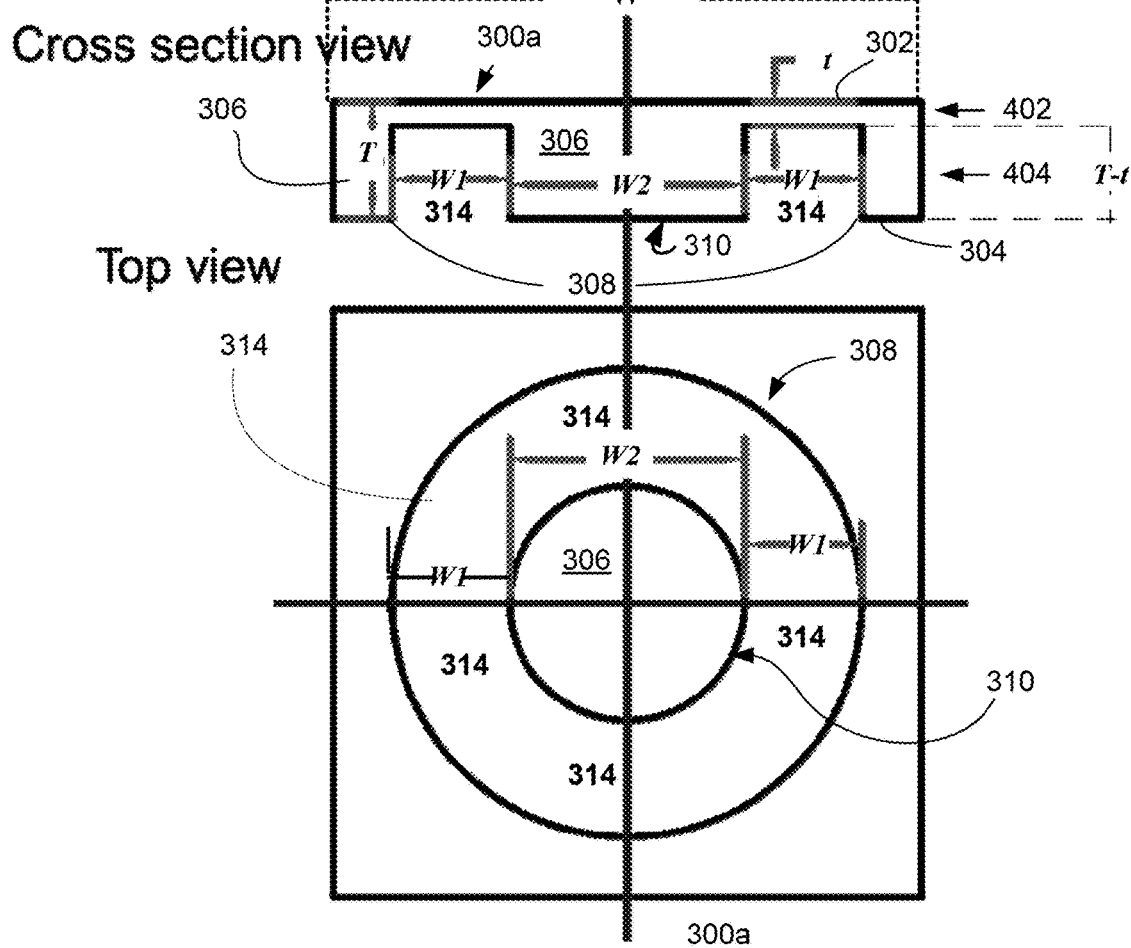
FIG. 4 shows a design of a notch ring structure for specific cell picking from a plastic device. (A) A cross-section view and top view of a notch ring: The symbol W1 is the width of groove of the notch structure, T is the total thickness of the substrate of the device, t is the notch structure's bottom thickness (viewed from the bottom of the device), W2 is the width of the objects (target substrate) to be picked. (B) A fabricated plastic substrate (middle panel) containing notch ring structures on its back surface. The enlarged images of the circular notch rings and the fractured surface of the dish after picking (left and right panels).
Figure 4:
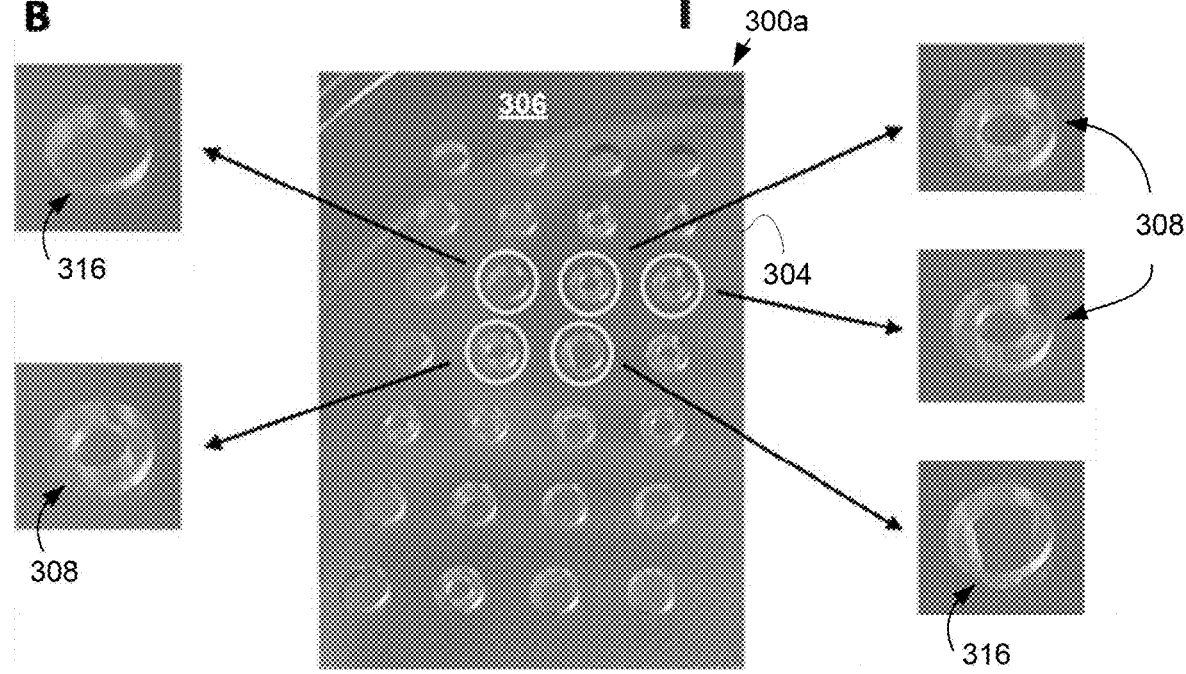

FIGS. 3 and 4 show the concept of a substrate design the process for transferring cells from devices made of hard material (e.g. Plastic). Referring to FIG. 3, device (300a, 300b, 300c, or 300d) that is made to have notch ring structures 308 (3 notch ring structures 308a, 308b, 308c illustrated) is made of hard plastic martial 306. The target particles 104 on a flat substrate in device 300a or 300c (A & C) or on a multi-well substrate in device 300b, 300d (B & D) are selectively pick out and transferred by inserting a pair of tweezers 312 to gripe a portion 310 of the substrate 306, break it and remove it from device. Side-view of the device. A tool (e.g., a pair of tweezers 312) to hold the target unit 310. The substrate 306 of the device is made out of a hard material. The target particles may be located inside a closed channel or chamber (C &D). Device C and Device D each have a cover substrate 330 so that the target particles are enclosed. The cover substrate 330 may be made of the same material as substrate 306.

The notch structure is used to facilitate the alignment of the tweezers, and also provides a mechanical weak point to allow the substrate to fracture at a desired so the cells within that location will be transferred from the device. A target cell transferring device 300a, 300b, 300c, or 300d may comprises:

(a) a substrate 306 with a thickness of T and a width of W, having a top portion 402 with a thickness oft and a bottom portion 404 with a thickness of T-t immediately adjacent to the top portion, the top portion 402 having a top surface 302 and the bottom portion 404 having a bottom surface 304 opposite to the top surface 302;

(b) a notch structure 308 formed in the bottom portion 404 of the substrate 306, comprising: a circle-shaped or C-shaped groove 314 with a width of W1, located at a distance oft below the top surface 302 of the substrate 306, wherein the groove 314 is formed in the bottom portion 404 from the bottom surface 304 extending toward the top portion 402; and (c) a target substrate portion 310 with a width of W2 and a thickness of T, located in the top and bottom portions of the substrate 306 and being surrounded by the circle-shaped or C-shaped groove 314;

wherein the substrate 306 width W is greater than the summation of the width W2 of the target substrate portion 310 and the double groove width 2×W1.

FIG. 4 shows a notch structure 308 design and device which was used to demonstrate the selective removal of an area of the substrate from a petri dish device 300a. The width W1 of the circular notch ring was at least 200 μm in order to allow the tweezers' tips to be inserted into the notch groove. The depth of notch depends on the substrate's thickness and rigidity. A cross-section view and top view of a notch ring 308 are shown (A). The symbol W1 is the width of groove 314 of the notch structure 308, T is the total thickness of the substrate of the device 300a, t is the notch structure's bottom thickness (viewed from the bottom of the device), W2 is the width of the objects 310 (target substrate) to be picked. It was demonstrated that the notch structure design allowed successful selective removals of an area of the substrate from a petri dish device 300a (B). A fabricated plastic substrate (B, middle panel) containing notch ring structures 308 on its back surface 304 is shown (viewed from the bottom surface of the device 300a). The enlarged images (left and right panels) show the circular notch rings 308 and the fractured surface 316 (i.e., the bottom surface where a notch structure was removed) of the dish 300a after picking.

Figure 5:
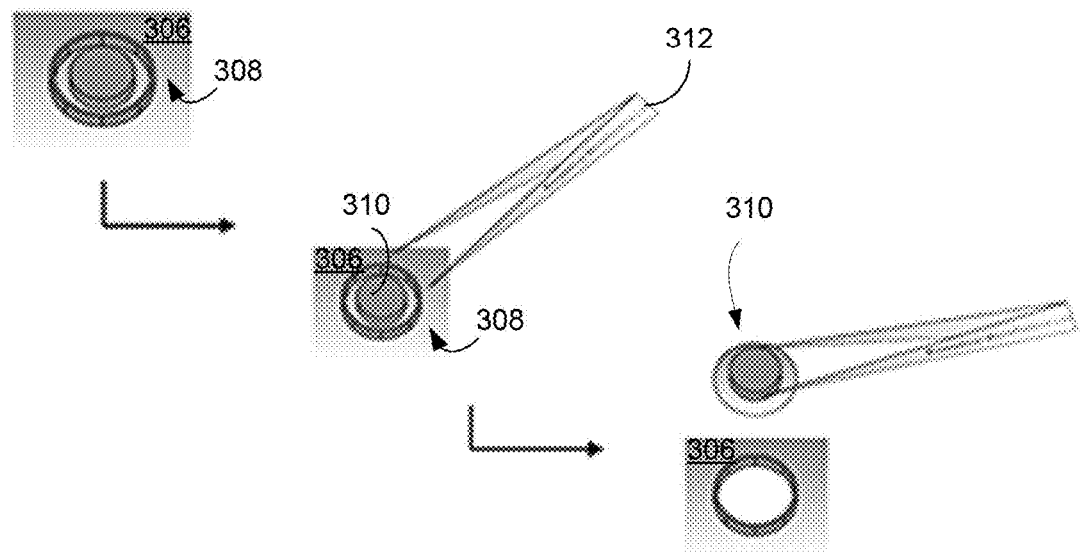
FIG. 5 shows removal of a target unit from a plastic substrate. (A) a schematic drawing showing an operation workflow of a target picking process. (B) Successful picking of a target unit by a pair of tweezers from a fabricated plastic Petri dish whose bottom surface has notch rings of various design dimensions.
Figure 5:
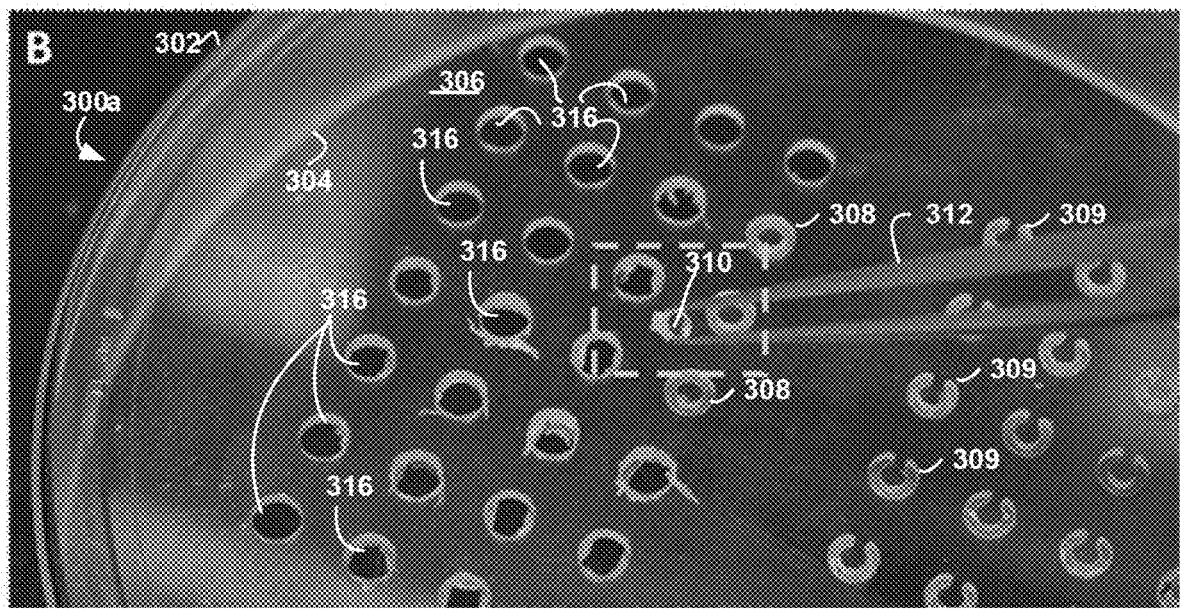

FIG. 5 shows removal of a target unit 310 from a plastic substrate 306. Successful picking of a target unit 310 by a pair of tweezers 312 from a fabricated plastic Petri dish 300a whose bottom surface 304 has notch rings 308 (circle shaped), 309 (C-shaped) of various design dimensions. It was demonstrated that the circular notch ring design 308 and selective substrate removals can be used on a plastic dish, which is made of polystyrene with a bottom plate thickness T of 1 mm. The results showed that we could fabricate a non-through notch 308, 309 with an appropriate depth T-t (>600 μm) that not only maintains an intact surface 302, but also allows for the intended selective removals of the substrate 310 from the device 300a. Note that, after the selective removal of a substrate area (i.e., target substrate 310), the remaining substrate area 306 stayed intact (B). This proves the feasibility of using this method for selective cell transfers from a device made of a hard plastic material.

Cells were Transferred Successfully and Maintained their Growth Capability

Figure 6:
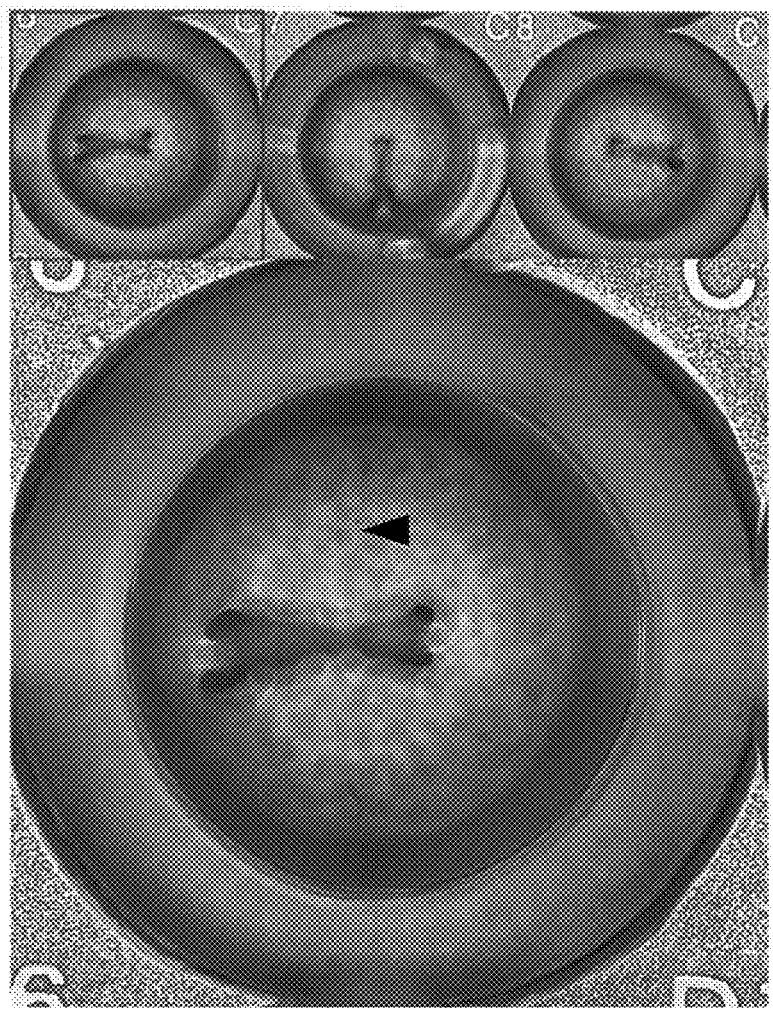
FIG. 6. shows photographs of PDMS plugs placed inside a 96-well plate, where the transferred cells could attach and proliferate inside the wells of the 96-well plate (arrowhead) after 7 day.
Figure 7:
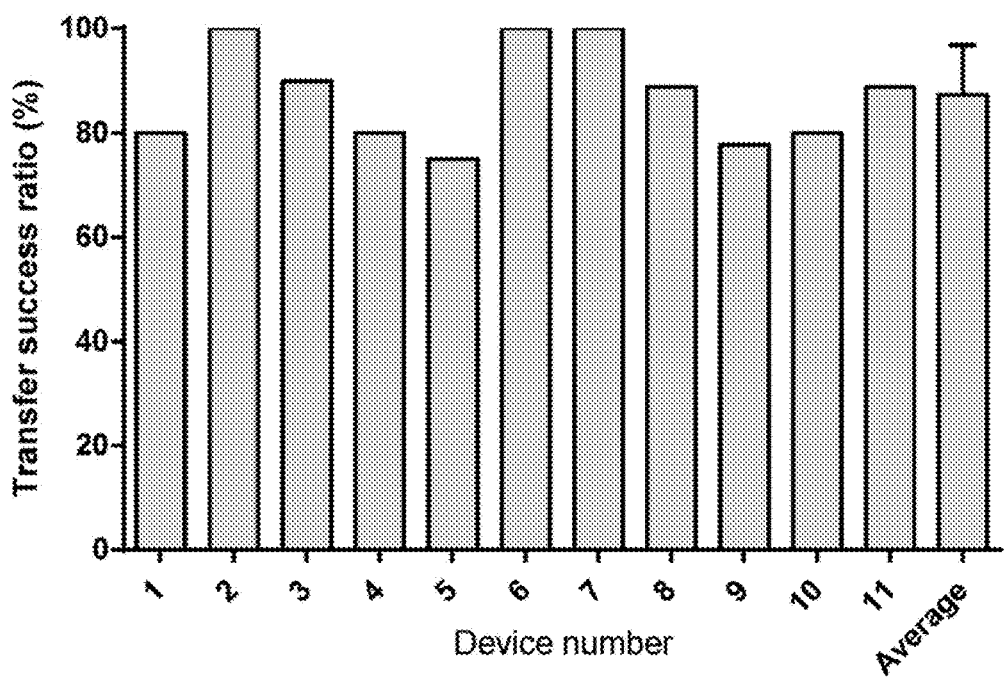
FIG. 7 is a graph showing the successful rate (i.e., clone growth efficiency) of the cell growth in the cells transferred from a PDMS device, in which the device number refers to the sample number.

FIG. 6 shows cell growth in a 96 well-plate after being transferred from a PDMS device. The cells which were released from PDMS plugs attached onto the well plate's substrate (arrowhead) and showed normal morphology. To understand how cells grow in a 96 well-plate after cell transfer from the PDMS device, we analyzed the number of cells in each well of the 96 well-plate for 10 days. For each well, if the cell number increased, the well would be counted as being a positive data point (i.e., cells can proliferate in the well plate after cell transfer). For every PDMS device, cells on 3 to 12 punched plugs were each transferred to the a well of a well plate. Our result showed that most of the transferred cells continued to proliferate at an efficiency of 87.32±9.47% (FIG. 7). Our demonstration shows that the cell transfer method has a high success rate and does not affect cell survival and growth.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of transferring a target particle from one device to another device, comprising:
    providing a target particle transferring device, wherein the target particle transferring device comprises:
        a substrate with a thickness of T and a width of W, having a top portion with a thickness of t, which is smaller than the thickness of T, and a bottom portion with a thickness of T-t immediately adjacent to the top portion, the top portion having a top surface and the bottom portion having a bottom surface opposite to the top surface;
        a notch structure formed in the bottom portion of the substrate, comprising a groove with a width of W1, located at a distance of t below the top surface of the substrate, wherein the groove is formed in the bottom portion from the bottom surface extending toward the top portion;
        a target substrate portion with a width of W2 and a thickness of T, wherein the target portion of the substrate has a well having a depth of d that is smaller than the substrate thickness T; and
        a particle of interest inside the well and attached onto the target substrate portion;
    using a tool to remove the target substrate portion away from the target particle transferring device along with the particle of interest attached thereto; and
    placing the removed target substrate portion along with the particle of interest attached thereto into a container.

2. The method of claim 1, wherein the target substrate portion with the particle of interest attached thereto is removed from the target particle transferring device by using the tool to grip the target substrate portion from the groove of the notch structure.

* * * * *